US00PP26022P3

(12) United States Plant Patent
Nir

(10) Patent No.: US PP26,022 P3
(45) Date of Patent: Oct. 27, 2015

(54) *CHAMELAUCIUM* PLANT NAMED 'FIRST MAYA'

(50) Latin Name: ***Chamelaucium uncinatum*× *megalopetalum***
Varietal Denomination: FIRST MAYA

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 113 days.

(21) Appl. No.: 13/986,495

(22) Filed: May 7, 2013

(65) Prior Publication Data

US 2014/0338082 P1 Nov. 13, 2014

(51) Int. Cl.
*A01H 5/02* (2006.01)

(52) U.S. Cl.
USPC ..... Plt./229
CPC ..... *A01H 5/02* (2013.01)

(58) Field of Classification Search
USPC ..... Plt./229
CPC ..... A01H 5/00
See application file for complete search history.

(56) References Cited

PUBLICATIONS

Nir Nursery, "Characteristics of Wax Flower varieties", retrieved from the internet Sep. 22, 2014 at <http://www.nir.co.il/characteristics-of-wax-flower-varieties>.*
UPOV 'Record Detail', retrieved from UPOV website Sep. 22, 2014.*

* cited by examiner

*Primary Examiner* — Keith O. Robinson
(74) *Attorney, Agent, or Firm* — Cassandra Bright

(57) ABSTRACT

A new and distinct *Chamelaucium* cultivar named 'FIRST MAYA' is disclosed, characterized by medium sized, creamy white colored flowers. The new variety is very early blooming. The new variety is a *Chamelaucium*, normally producing cut flower stems, or as a garden or container plant.

1 Drawing Sheet

Latin name of the genus and species: *Chamelaucium uncinatum*×*megalopetalum.*

Variety denomination: 'FIRST MAYA'.

BACKGROUND OF THE INVENTION

The new *Chamelaucium* cultivar is a product of chance discovery by the inventor, Nitzan Nir, in Kfar Hess, Israel. The new variety was selected as a naturally occurring whole plant mutation of the variety *Chamelaucium uncinatum*× *megalopetalum* 'Early Maya', unpatented. 'First Maya' was selected during October of 2009, at a commercial nursery in Kfar Hess, Israel.

Asexual reproduction of the new cultivar has been performed by vegetative cuttings. This was first performed at a commercial nursery in Kfar Hess, Israel in December of 2010 and has shown that the unique features of this cultivar are stable and reproduced true to type in successive generations.

SUMMARY OF THE INVENTION

The cultivar 'FIRST MAYA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FIRST MAYA'. These characteristics in combination distinguish 'FIRST MAYA' as a new and distinct *Chamelaucium* cultivar:

1. Very early blooming season beginning in September in the Northern Hemisphere.

2. Creamy white flower.
3. Medium flower size.
4. Pink flower bud.

PARENT COMPARISON

Plants of the new cultivar 'FIRST MAYA' are similar to plants of the parent, *Chamelaucium uncinatum*×*megalopetalum* 'Early Maya' in most horticultural characteristics, however, plants of the new cultivar 'FIRST MAYA' produce larger flowers one month earlier than the parent. Additionally, flower buds of 'FIRST MAYA' are darker than flower buds of 'Early Maya'.

COMMERCIAL COMPARISON

Plants of the new cultivar 'FIRST MAYA' are comparable to the variety *Chamelaucium* hybrid 'Blondie', U.S. Plant Pat. No. 9,966. The two *Chamelaucium* varieties are similar in most horticultural characteristics; however, the new variety 'FIRST MAYA' begins flowering earlier than 'Blondie'. Flower buds of 'FIRST MAYA' are Red 50A compared to bud color of Red-Purple 60A of 'Blondie'. Additionally, 'FIRST MAYA' petals are slightly brighter white, and not occasionally blushed with pink, as characteristic of 'Blondie'.

Plants of the new cultivar 'FIRST MAYA' can also be compared to the commercial variety *Chamelaucium uncinatum* 'Guy', unpatented. These varieties are similar in most horticultural characteristics; however 'FIRST MAYA' flowers earlier than 'Guy'. Additionally, petals of the variety 'Guy' can change from white to pink, whereas petals of 'FIRST MAYA' are consistently white. Flower buds of 'Guy' are lighter red than flower buds of 'FIRST MAYA'.

BRIEF DESCRIPTION OF THE PHOTOGRAPH

The accompanying photograph in FIG. 1 illustrates in full color a close up of typical flowers and foliage of 'FIRST MAYA'. The age is approximately 1 year. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'FIRST MAYA' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum×megalopetalum* 'FIRST MAYA'.

Age of plant described: At least 2 months old from a rooted cutting.

Typical flowering stems harvested per plant: 100 to 120 during the course of the season.

Vase life of flowers: Two weeks.

PROPAGATION

Time to produce a rooted plantlet: 30 to 60 days at approximately 24° C.

Root description: Fibrous.

PLANT

Growth habit: Upright plant produces multiple stems from a pinch, or after harvesting stems.

Height: 150 cm.

Plant spread: 50 cm.

Growth rate: Rapid.

Branching characteristics: Moderate branching occurs after pinching.

Length of primary lateral branches: 60 cm on average.

Diameter of lateral branches: 0.3 cm.

Quantity of primary lateral branches: 100 to 120. These are the harvested flowering stems.

Characteristics of primary lateral branches:

- *Form*.—Round.
- *Diameter*.—0.4 cm.
- *Color*.—Near RHS Yellow-Green 152B over Grey-Grown 199A.
- *Texture*.—Smooth.
- *Strength*.—Stems brittle.

Internode length: Range from 0.5 to 6 cm.

FOLIAGE

Leaf:

- *Arrangement*.—Opposite.
- *Quantity*.—Approximately 10 leaves, in the 10-15 cm section from the top of the branch.
- *Average length*.—0.8 cm.
- *Average width*.—0.1 cm.
- *Shape of blade*.—Needle.
- *Apex*.—Acute.
- *Base*.—Attenuate.
- *Margin*.—Entire.
- *Texture*.—Glabrous all surfaces.
- *Pubescence*.—None.
- *Aspect*.—Straight, occurring at approximately a 15 to 30 degree angle.
- *Color*.—Young foliage: RHS Yellow-Green 146C. Mature foliage: RHS Yellow-Green 146B. Venation: Indistinguishable from foliage.
- *Petiole*.—Not present.

FLOWER

Natural flowering season: Plants planted during April through October begin flowering September through January, without a juvenility period in Kfar Hess, Israel. Plants flower continuously under short day conditions.

Days to flowering from rooted cutting: Approximately 60 days.

Inflorescence type: Terminal Panicle.

Individual flower type: Single, rotate 5 petaled with a cone shaped hypanthium. Flowers outwardly facing.

Persistent or self-cleaning: Self-Cleaning.

Lastingness: Up to 14 days in a vase. Approximately 45 to 60 days on the plant.

Typical flowering stem length: Approximately 60 cm.

Bud:

- *Shape*.—Spherical.
- *Length*.—0.5 cm.
- *Diameter*.—0.5 cm.
- *Color*.—Near RHS Red 50A.

Inflorescence size:

- *Diameter*.—Average 12 cm.
- *Length*.—Average 22 cm.

Flower size:

- *Diameter*.—Average 1.2 cm.
- *Length*.—Average 1.3 cm.

Corolla:

- *Petals*.—Arrangement: Rotate, not overlapping. Length: Average 0.7 cm. Diameter: Average 0.7 cm. Quantity: 5. Texture: Smooth. Apex: Obtuse rounded. Base: Fused into a hypanthium.
- *Color*.—When opening: Upper surface: Near RHS White 155B. Lower surface: Near RHS White 155B. Fully opened: Upper surface: Near RHS White 155B. Lower surface: Near RHS White 155B. Aging: Upper surface: Near RHS White 155C. Lower surface: Near RHS White 155C.

Hypanthium:

- *Diameter*.—Average 0.7 cm.
- *Length*.—Average 0.4 cm.
- *Shape*.—Obconical.
- *Color*.—When opening: Inner surface: Near RHS Green-White 155D, blotched Red 53B. Outer surface: Near RHS White 155B. Fully opened: Inner surface: Near RHS Green-White 155D, blotched Red 53B. Outer surface: Near RHS White 155B. Aging: Inner surface: Near RHS Green-White 155D, blotched Red 53B. Outer surface: Near RHS White 155B.

Calyx/sepals:

- *Quantity per flower*.—Fused into a single, conical structure.
- *Length*.—0.4 cm.
- *Width*.—0.7 cm.
- *Margin*.—Entire, incised approximately 2 mm.
- *Texture*.—Smooth.

*Color*.—Near RHS Yellow-Green 144A, apex White 155A.

Peduncle: Peduncle consists of the plant stem.

Pedicel:

*Length*.—0.6 cm.

*Diameter*.—0.1 cm.

Fragrance: None.

REPRODUCTIVE ORGANS

Stamens:

*Number*.—10.

*Filament length*.—1 mm.

*Filament color*.—Near RHS White 155C.

Anthers:

*Shape*.—Oval.

*Length*.—0.25-0.5 mm.

*Width*.—0.2 mm.

*Color*.—Near RHS Greyed-Orange 163A.

Pollen: Not observed to date.

Pistil:

*Number*.—1.

*Length*.—0.5 cm.

*Length*.—0.8 cm.

*Color*.—Near RHS White 155A.

*Style color*.—Near RHS White 155A.

*Stigma*.—Shape: Round. Color: Near RHS Greyed-White 156A. Texture: Glabrous.

OTHER CHARACTERISTICS

Seeds and fruits: Single flower produces one fruit. Fruits are not fertile. Fruit type is a nut, colored near Grey-Brown N199A, seed is unwinged colored approximately 1.5 mm, brown in color, too minute to accurately measure color with RHS chart.

Disease/pest resistance: Neither resistance nor susceptibility to the normal diseases and pests of *Chamelaucium* have been observed to date.

Temperature tolerance: From −2° C. to 35° C.

Drought tolerance: Very good tolerance for drought.

What is claimed is:

1. A new and distinct cultivar of *Chamelaucium* plant named 'FIRST MAYA' as herein illustrated and described.

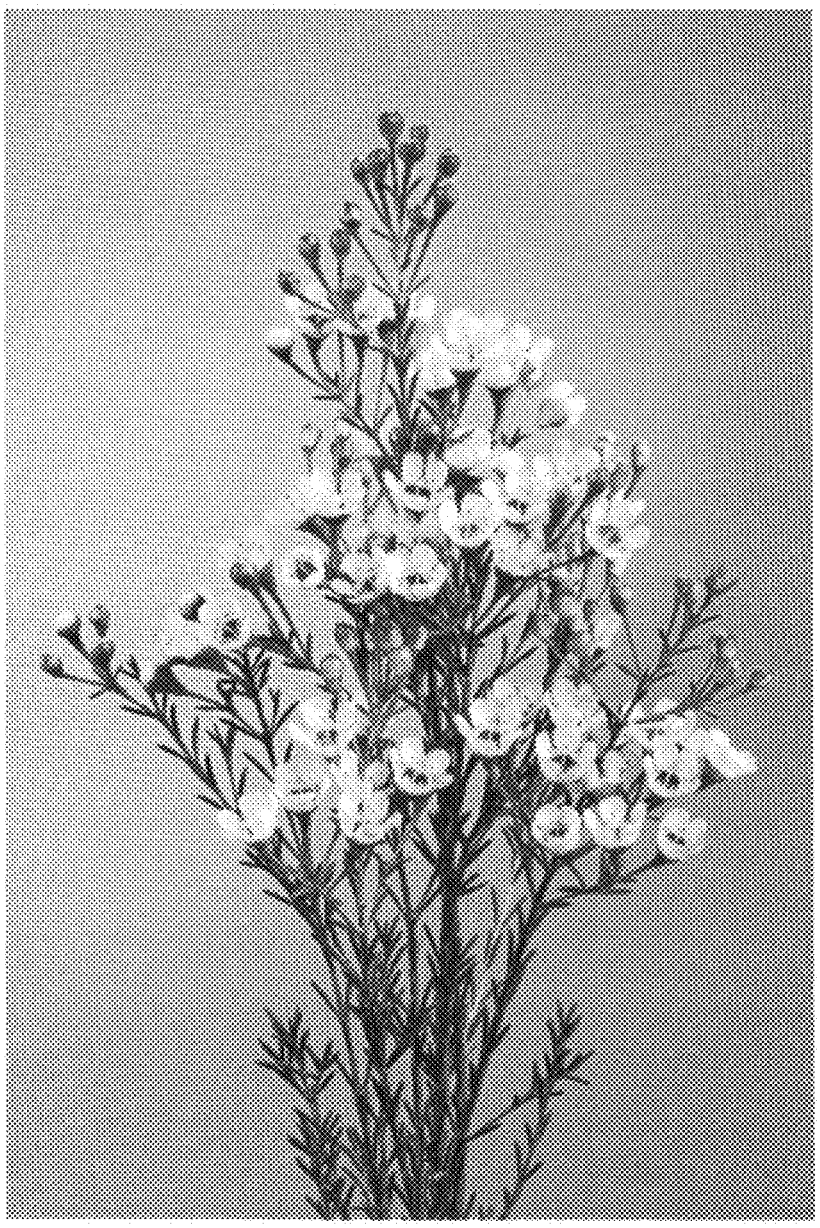

* * * * *